US009011387B2

(12) United States Patent
Ekman et al.

(10) Patent No.: US 9,011,387 B2
(45) Date of Patent: Apr. 21, 2015

(54) FORCE TRANSMISSION ARRANGEMENT FOR AUTO-INJECTOR

(75) Inventors: Matthew Ekman, Macclesfield (GB); Timothy Donald Barrow-Williams, Herts (GB); Thomas Mark Kemp, Ashwell (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 380 days.

(21) Appl. No.: 13/580,146

(22) PCT Filed: Feb. 16, 2011

(86) PCT No.: PCT/EP2011/052305
§ 371 (c)(1),
(2), (4) Date: Feb. 11, 2013

(87) PCT Pub. No.: WO2011/101383
PCT Pub. Date: Aug. 25, 2011

(65) Prior Publication Data
US 2013/0204195 A1 Aug. 8, 2013

(30) Foreign Application Priority Data
Feb. 22, 2010 (EP) .................................... 10154192

(51) Int. Cl.
*A61M 5/20* (2006.01)
*A61M 5/32* (2006.01)
(Continued)

(52) U.S. Cl.
CPC ........... *A61M 5/3158* (2013.01); *A61M 5/2033* (2013.01); *A61M 5/315* (2013.01);
(Continued)

(58) Field of Classification Search
CPC ................. A61M 2005/206; A61M 2005/208; A61M 2005/2086; A61M 2005/2418; A61M 5/20; A61M 5/2033; A61M 5/315; A61M 5/3158

USPC .......................... 604/187, 192, 197, 220, 228
See application file for complete search history.

(56) References Cited

U.S. PATENT DOCUMENTS 5,137,516 A * 8/1992 Rand et al. ..................... 604/136
5,318,584 A * 6/1994 Lange et al. ................... 606/182
(Continued)

FOREIGN PATENT DOCUMENTS

| WO | 0189613 A1 | 11/2001 |
| WO | 2004107975 A2 | 12/2004 |

(Continued)

OTHER PUBLICATIONS

International Preliminary Report on Patentability for Int. App. No. PCT/EP2011/052305, mailed Sep. 7, 2012.

*Primary Examiner* — Quynh-Nhu H Vu
(74) *Attorney, Agent, or Firm* — McDonnell Boehnen Hulbert & Berghoff LLP

(57) ABSTRACT

The invention relates to a transmission arrangement for controlling a force of a translation, the transmission arrangement comprising a drive collar (13) connectable to a translative drive means (11) and prevented from rotating with respect to a ground (12) of the drive means (11), a flange face of the drive collar (13) bearing against a mating flange face of a friction collar (20), the friction collar (20) slidable in longitudinal direction and rotationally constrained by engagement in a cam track (12.3), another flange face of the friction collar (20) bearing against a mating flange face of a plunger (8), the plunger (8) slidable in longitudinal direction and prevented from rotating.

15 Claims, 9 Drawing Sheets

(51) Int. Cl.
*A61M 5/315* (2006.01)
*A61M 5/46* (2006.01)
*A61M 5/48* (2006.01)
*A61M 5/24* (2006.01)
*A61M 5/31* (2006.01)

(52) U.S. Cl.
CPC ............ *A61M 5/3202* (2013.01); A61M 5/326 (2013.01); *A61M 5/46* (2013.01); *A61M 5/482* (2013.01); *A61M 5/484* (2013.01); *A61M 2005/206* (2013.01); *A61M 2005/208* (2013.01); *A61M 2005/2086* (2013.01); *A61M 2005/2418* (2013.01); *A61M 2005/3103* (2013.01); *A61M 2005/3152* (2013.01); *A61M 2005/3247* (2013.01); *A61M 2205/581* (2013.01); *A61M 2205/583* (2013.01); A61M 5/20 (2013.01)

(56) References Cited

U.S. PATENT DOCUMENTS

| | | |
|---|---|---|
| 2002/0007142 A1 * | 1/2002 | Hjertman et al. ............... 604/38 |
| 2002/0095120 A1 | 7/2002 | Larsen et al. |
| 2010/0049125 A1 * | 2/2010 | James et al. ................... 604/110 |
| 2012/0184917 A1 * | 7/2012 | Bom et al. ..................... 604/187 |

FOREIGN PATENT DOCUMENTS

| | | |
|---|---|---|
| WO | 2007002052 A2 | 1/2007 |
| WO | 2008112472 A2 | 9/2008 |
| WO | 2009141650 A2 | 11/2009 |

* cited by examiner

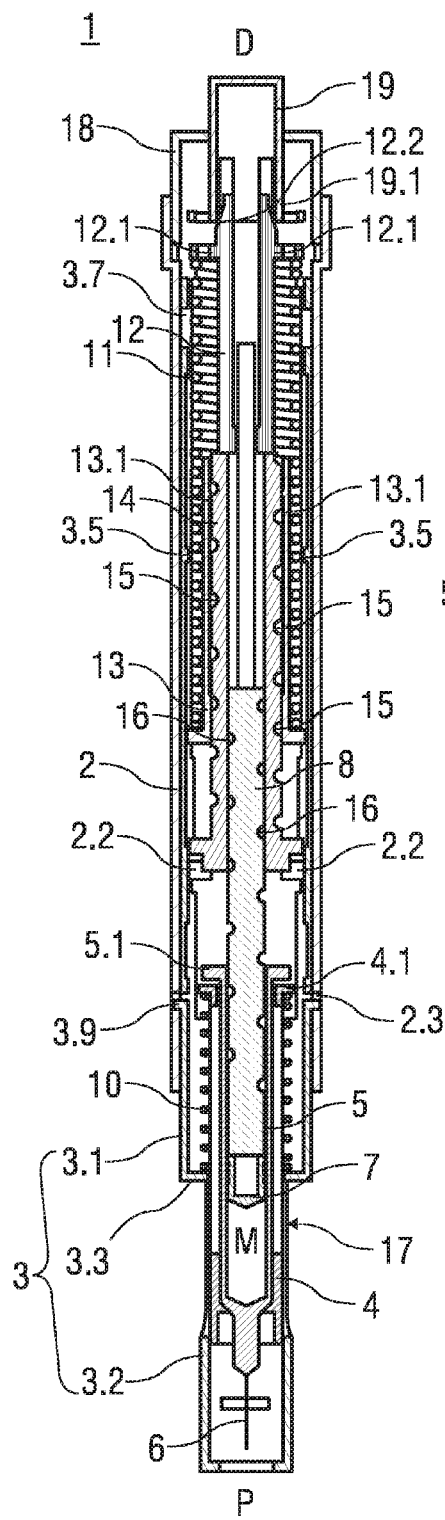
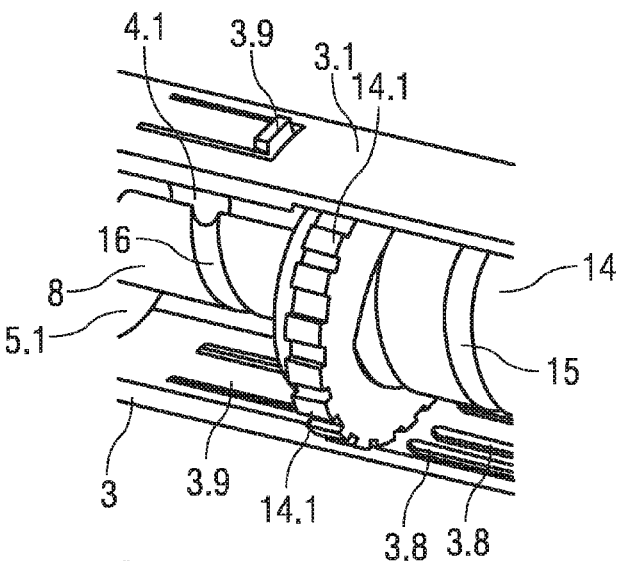
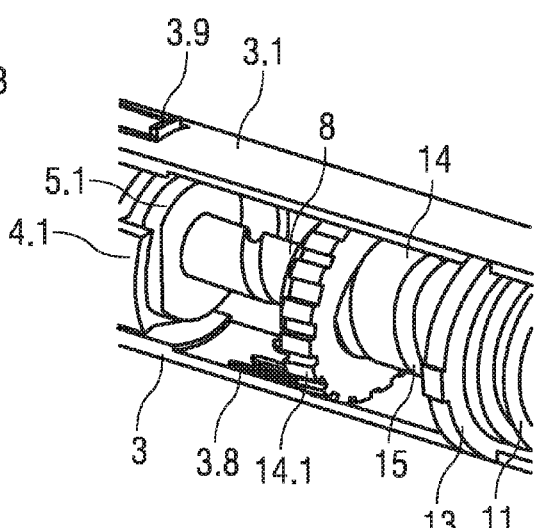
FIG 7A
FIG 7B
FIG 7C

FORCE TRANSMISSION ARRANGEMENT FOR AUTO-INJECTOR

CROSS REFERENCE TO RELATED APPLICATIONS

The present application is a 35 U.S.C. 371 National Application of PCT/EP2011/052305 filed Feb. 16, 2011, which claims priority to European Patent Application No. 10154192.8 filed Feb. 22, 2010, and, the entire contents of which are incorporated entirely herein by reference.

TECHNICAL FIELD

The invention relates to a transmission arrangement for controlling a force of a translation, in particular for application in an auto-injector for delivering a dose of a liquid medicament.

BACKGROUND OF THE INVENTION

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages for the user from this approach. If the user stops pressing the button/plunger, then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Forces required of the user/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

Auto-injectors may be disposable or single use devices which may only be used to deliver one dose of medicament and which have to be disposed of after use. Other types of auto-injectors may be reusable. Usually they are arranged to allow a user to load and unload a standard syringe. The reusable auto-injector may be used to perform multiple parenteral drug deliveries, whereas the syringe is disposed after having been spent and unloaded from the auto-injector. The syringe may be packaged with additional parts to provide additional functionality.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, energy stored in the tension spring is released and the injection needle is automatically retracted back to its original storage position.

When an auto-injector is driven by a spring, the spring force is usually highest at the beginning of the motion. With increasing extension of the spring the spring force decays. This may lead to variation in the delivery of the dose over the injection cycle.

WO 2004/107975 A2 discloses a device for fluid delivery. The device comprises a cartridge having a plurality of cavities and a plurality of penetrating members. The plurality of penetrating members are each at least partially contained in cavities of the cartridge wherein the penetrating members are slidably movable to extend outward from openings on said cartridge to penetrate tissue. Each of the penetrating members comprises a needle with a lumen coupled to a canister containing a material to be injected.

WO 01/89613 A1 discloses an injector device for delivery of liquid from a high pressure, the device comprising a housing, a pressure chamber comprising a pressure barrel for accommodation of at least one piston therein and having a front end opening for ejection of the liquid, the pressure chamber being of sufficient strength to sustain the liquid pressure. The device further comprises a storage chamber, separate from the pressure chamber, for the liquid or the liquid precursor components, and a conduit between the pressure chamber and the storage chamber. A pressurizing mechanism in the housing is arranged to apply force, directly or indirectly, on the piston in the pressure barrel to create said liquid pressure. The pressure chamber, the piston and at least a part of the conduit is arranged as a unit, wherein said unit and the housing have corresponding fitting parts allowing releasable attachment of the unit to the housing in a position permitting fluid connection between storage chamber and pressure chamber through the conduit and permitting the pressurizing mechanism to act on the piston.

WO 2007/002052 A2 discloses a method and apparatus for administering a pharmaceutical. The method employs a delivery device including a housing, a pharmaceutical containing needled syringe movable within the housing, an activation button disposed at one of the housing, and wherein the housing is flared radially outward at the other end and designed to allow visibility of the needled syringe. A skin-contacting surface of the housing at the flared end is designed to limit slippage along the skin, and at least one injection targeting guide is provided. When the device is sited for injection, and without pressing the delivery device housing toward the injection site with any predetermined force by the one hand holding the housing, the activation button may be plunged with the other hand toward the housing to trigger an advancing assembly within the device that first automatically advances the needled syringe to insert a needle into the injection site, and that second automatically advances the syringe piston to force pharmaceutical through the inserted needle.

WO 2008/112472 A2 discloses a delay mechanism for staging the operation of an automatic injection apparatus to ensure medication contents are properly delivered prior to the needled syringe of the apparatus being retracted. In one form, the delay mechanism includes a shuttle, a follower, a locking member, a damping compound, and a driver and a driver biasing element. The shuttle is for a needled syringe of the apparatus and includes a first latching element. The follower includes a second latching element and a cammable surface, which second latching element is for cooperating with the first latching element to limit motion of the shuttle relative to the follower in a second direction opposite the first direction. The locking member is movable from a locking position to a release position by engagement with the syringe plunger during an injection, the locking member, when in the locking position, preventing rotation of the follower relative to the shuttle, the locking member, when in the release position, allowing rotation of the follower relative to the shuttle. The damping compound is between the follower and a supporting surface to dampen rotation of the follower relative to the shuttle. The driver is rotatably fixed relative to the shuttle and includes a camming surface. The driver biasing element is for forcing the driver from a first position to a second position when the locking member moves to the release position, whereby during movement of the driver to the second position, the driver camming surface engages the follower cammable surface to force the follower to rotate relative to the shuttle from a latching position, at which the first and second latching elements cooperate, to an unlatching position, at which the second latching element is disengaged from the first latching element to allow movement of the shuttle for retracting the syringe needle into the housing of the automatic injection apparatus after injection.

U.S. Pat. No. 5,318,584 A discloses a blood lancet device for withdrawing blood for diagnostic purposes, in which with the aid of a lancet drive in a housing a lancet holder with a lancet positioned in it and moveable along a predetermined, straight puncture path is moved until the tip of the lancet emerges from the outlet, in order to produce a wound in a body part adjoining the outlet. The lancet holder also serves to retract the lancet into a position in which the tip is again positioned within the housing. In order to make possible a puncture involving especially little pain, the lancet drive has a rotary/sliding transmission system whose input side is formed by a transmission member which is rotatable about an axis of rotation parallel to the predetermined puncture path. This input-side transmission member of the rotary/sliding transmission system is coupled with the elastic drive element of the lancet drive and converts a torque transmitted to the transmission member into a longitudinal displacement in the direction of the predetermined puncture path, which is transmitted to the lancet holder.

SUMMARY OF THE INVENTION

It is an object of the present invention to provide a means for adapting the force available from a translative drive means to a desired output force.

The object is achieved by a transmission arrangement according to claim 1.

Preferred embodiments of the invention are given in the dependent claims.

According to the invention a transmission arrangement serves for controlling a force of a translation. The transmission arrangement comprises a drive collar connected to a translative drive means and prevented from rotating with respect to a ground of the drive means which may be a housing or chassis or a grounding member fixed thereto. A flange face of the drive collar bears against a mating flange face of a friction collar. The friction collar is slidable in longitudinal direction and rotationally constrained by engagement in a cam track. Another flange face of the friction collar bears against a mating flange face of a plunger. The plunger is slidable in longitudinal direction and prevented from rotating.

The plunger is the component for outputting the translation modified by the transmission arrangement.

Rotation of the friction collar is defined by a pitch angle of the cam track. The load on the friction collar is coupled to the rotationally fixed, axially free plunger. The force of the drive means acting on both mating surfaces of the friction collar towards the drive collar and towards the plunger introduces a friction force opposing rotation. As the friction collar axially translates, it is forced to rotate by any section of the cam track that is not parallel with a longitudinal axis. The friction collar will only rotate if the friction force between the mating surfaces of the drive collar and the plunger is overcome. The torque to overcome this friction force is generated by the contact force between the cam follower and the cam track, in which the cam follower is engaged. The contact force is generated by the spring force of the drive spring. A degree of coupling between the spring force and the contact force is defined by the respective pitch angle of the cam track. By an appropriate modification to the cam track angle, the amount of spring force required to overcome the friction force can be modified. For instance, increasing the cam angle requires more of the spring force to be reacted through the cam track, thereby reducing the force of the translation. The friction force is zero in straight sections of the cam track in parallel with a longitudinal axis of the overall arrangement. With any non-zero pitch angle the friction force is introduced.

When applied in an auto-injector with a compression spring as the drive means, the transmission arrangement can be used to modify an amount of spring force that is transmitted to a syringe or a stopper of the syringe.

Thus the spring force may be softened at the beginning of an injection cycle when the spring force is highest in order to reduce impact loads experienced by components within the auto-injector. When applied directly to a glass syringe, the risk of breaking the glass by impact is remarkably reduced. Furthermore, user discomfort related to high impact loads is reduced. The dispense characteristics of the auto-injector may be varied, e.g. in order to provide a rapid needle insertion, which is believed to offer benefits in terms of reducing the amount of pain felt by the patient. Furthermore, by adapting the transmitted force the dose may be delivered more steadily and the repeatability of the time required for the injection cycle is improved. Otherwise, if the cycle times are highly variable between different auto-injectors of the same type, the user may be confused and make errors when delivering the injection. The force available from the drive means may be modified for particular operations of the device, e.g. steps in the operational cycle, such as operating a latch mechanism to trigger needle retraction, may require a higher force, so the transmission arrangement may be tailored to deliver the required force. Particularly with a compression spring used as the drive means the spring force decays with increasing extension of the spring. The transmission arrangement may be adapted to compensate that decay by a pitch angle converging towards a straight, longitudinal section of the cam track, so at the end of the movement the full force of the compression spring is available. Thus a dose delivery flow rate may be kept constant.

The drive means may be a compression spring arranged over a shaft of a grounding member. The drive collar and the friction collar may be arranged in series with the compression spring and grounding member. The cam track may be arranged in an external surface of the shaft and a cam follower for engaging in the cam track may be arranged on the friction collar.

Preferably the pitch angle of the cam track is varied over its length in order to achieve the desired force of the translation.

There may be more than one cam track on the ground member shaft, the different cam tracks with different pitch angle profiles, so the force control may be customized by selecting one of the cam tracks for engaging with the friction collar.

Instead of the planar flange faces the plunger, drive collar and friction collar may have profiled or curved flange faces. In this case, rotation of the friction collar would introduce additional force control by the varying angles of the mating faces. At the same time the distance traveled by the plunger may be increased or reduced relative to the motion of the drive collar by modifying an overall length of the drive collar, friction collar and plunger when the friction collar is rotated.

The friction collar and the shaft of the grounding member may be arranged to provide a ratchet feature to generate an audible user feedback when the friction collar advances. Small raised features can be spaced in the cam track over which the follower has to pass. These features can be profiled such that they induce vibration into the device as the dose is delivered.

In a preferred embodiment the plunger may comprise at least a hollow portion arranged for fitting onto the ground member shaft. Thus, the shaft serves for centring all components. The hollow portion may have apertures in order to avoid the generation of a vacuum in the hollow portion when the plunger is being pushed off the shaft during the translation.

The hollow portion of the plunger may comprise an internal cam follower for engaging in one of the straight, longitudinal sections of the cam track, thus preventing rotation of the plunger.

The transmission arrangement may be applied in an auto-injector for administering a dose of a liquid medicament. The auto-injector has a distal end and a proximal end with an orifice intended to be applied against an injection site, e.g. a user's skin.

In the context of this specification the term "proximal" refers to the direction pointing towards the patient during an injection while the term "distal" refers to the opposite direction pointing away from the patient. When referring to the proximal and distal portion of the auto-injector their respective distal and proximal ends are those that point in the respective direction during an injection.

The auto-injector further comprises:
an elongate housing arranged to contain a syringe with a hollow needle and a stopper for sealing the syringe and displacing the medicament, wherein the syringe is slidably arranged with respect to the housing,
a drive means capable of, upon activation:
  pushing the needle from a retracted position into an advanced position through the orifice and past the proximal end, and
  operating the syringe to supply the dose of medicament, and
activating means arranged to lock the drive means in a pressurized state prior to manual operation and capable of, upon manual operation, releasing the drive means for injection.

The transmission arrangement is arranged between the drive means and the syringe or the stopper in order to adapt the force of the compression springs to the requirements of an injection.

The drive means of the auto-injector is preferably arranged as a compression spring grounded at a distal end in a grounding member fixed to the housing, wherein a proximal end of the compression spring bears against the drive collar.

An intermediary component may be arranged for transmitting translation of the plunger to the syringe in order to first advance the syringe and needle while avoiding load onto the stopper thus avoiding wet injection, i.e. medicament leaking out of the needle's tip before the needle is fully inserted into the injection site. The intermediary component is furthermore arranged to be decoupled from the syringe when the needle has reached a predefined injection depth. At the same time the translation is coupled to the stopper in order to inject the dose.

In a preferred embodiment a shroud is arranged at least partially inside the housing. The shroud may be slidable in longitudinal direction between at least a retracted position, in which the needle is exposable and an advanced position, in which the needle is covered by the shroud. The shroud is arranged to be locked in the retracted position prior to manual operation of the activation means. Once the drive means has been released the shroud may be unlocked and automatically move towards the advanced position under load of a syringe spring. This automatic movement will happen when the auto-injector is removed from the injection site in the course of an injection or after the injection has been completed in order to hide the needle and keep the user from injuring themselves. As long as the user maintains the auto-injector pressed against the injection site during the injection cycle, the shroud will remain in the retracted position.

The shroud may be slidable from the retracted position in the distal direction into an unlocking position by a small distance against the bias of at least one flexural element which may be arranged at the shroud. Furthermore, interlocking means may be arranged to allow the activating means to be operated only, when the shroud is in the unlocking position, wherein the interlocking means are arranged to prevent the activating means from being operated otherwise. Thus, a skin interlock feature is provided for making sure, the auto-injector is properly positioned against the injection site before allowing the injection to be triggered by the user.

Usually the hollow needle is equipped with a protective needle shield for keeping the needle sterile and preventing it from being mechanically damaged. The protective needle shield is attached to the needle when the syringe or the auto-injector is assembled.

In order to prepare the auto-injector for delivering a dose the protective needle shield has to be removed from the needle.

In one embodiment a protective needle shield is attachable to the needle in a manner to partially protrude beyond the proximal end of the shroud through the orifice with the needle in its advanced position, which may be an "as shipped" state of the auto-injector. A syringe carrier may be arranged inside the shroud for holding the syringe, the syringe holder slidable with respect to the shroud. The syringe holder may comprise at least one resilient snap for locking it to the shroud in order to prevent relative axial motion. The snap may be arranged to be supportable from inside by the protective needle shield when the protective needle shield is attached to the needle in order to remain engaged with the shroud. The snap is inwardly biased to disengage from the shroud without support from inside in a manner to automatically disengage upon removal of the protective needle shield. Once the snap is disengaged, the syringe spring retracts the syringe carrier, the syringe and the needle into the retracted position with the needle hidden inside the shroud. In the state as shipped the auto-injector is needle safe due to the protective needle shield hiding the needle. With the syringe and needle retracting immediately upon removal of the protective needle shield the auto-injector remains needle safe when armed.

At least one resilient latch may be arranged on the shroud for engaging in a respective recess of the housing when the shroud is translated into its advanced position. Thus, post-injection needle safety is improved since the shroud cannot be pushed in distal direction again after the end of an injection cycle. In both cases, when the auto-injector is removed from the injection site during injection or after delivering the full dose the needle is covered and is needle safe.

In order to interlock the activation means or trigger button with the shroud at least one snap arm may be distally arranged at the drive collar in a manner to be engageable behind a shoulder on the grounding member in order to prevent expansion of the drive means. The snap arm may be disengageable from the shoulder by being pushed outward by a respective resilient extension of a trigger button. The resilient extension may be arranged to be flexed outward by pushing the trigger button in proximal direction thereby moving the resilient extension along a tapering surface of the grounding member which forces the resilient extension outwards. The shroud may be arranged to prevent at least one of the resilient extensions from flexing outwards when the shroud is its retracted position. At least one distal recess may be arranged in the shroud for allowing a respective resilient extension to be flexed outwards through the recess or aperture when the shroud is in an unlocking position.

The syringe spring may be arranged to bear against an internal shoulder in the shroud between a distal portion and a proximal portion and against a rear flange of the syringe carrier.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-desAsp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 7 is the auto-injector during removal from the injection site in the course of an injection.

Corresponding parts are marked with the same reference symbols in all figures.

DETAILED DESCRIPTION OF PREFERRED EMBODIMENTS

Figure 1A:
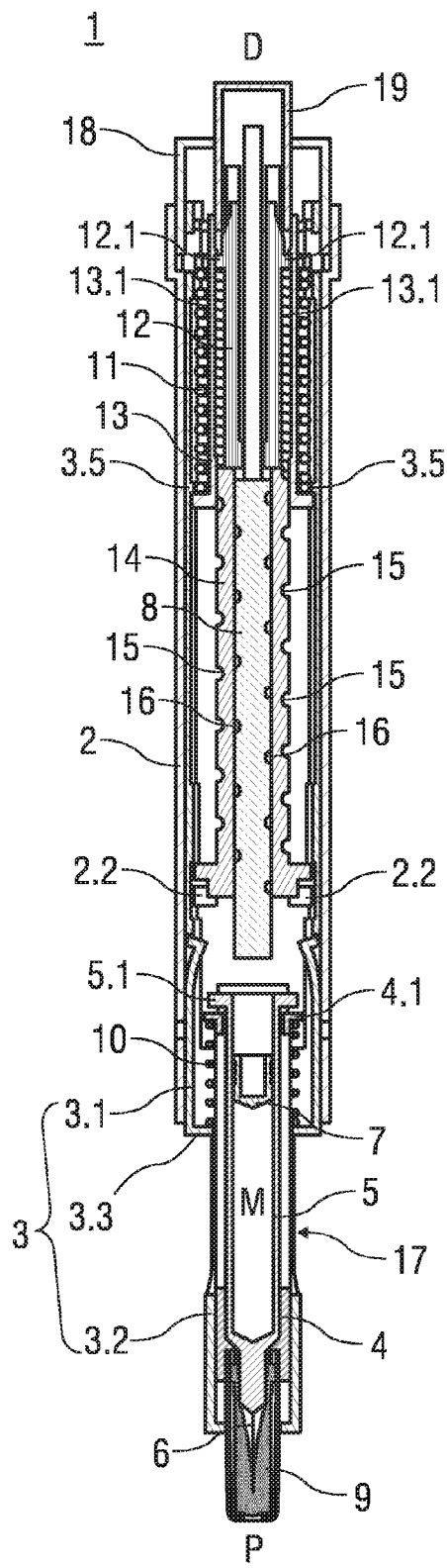
FIG. 1 are longitudinal sections in two section planes of an auto-injector with force control in an as shipped state.
Figure 1B:
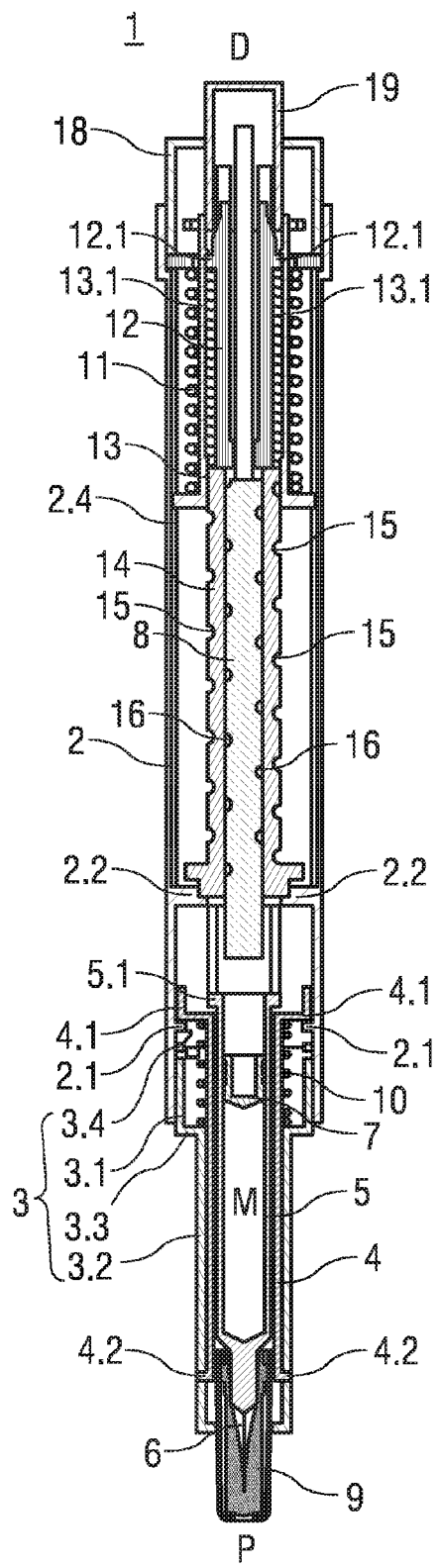

FIG. 1 shows two longitudinal sections in two section planes of an auto-injector 1 with force control in an as shipped state. The auto-injector 1 comprises an elongate housing 2, an essentially tubular shroud 3 arranged inside the housing 2 and slidable in longitudinal direction with respect to the housing 2. A distal portion 3.1 of the shroud has an external diameter selected to fit into the housing 2. The distal portion 3.1 extends essentially through the entire housing 2 to the distal end D. The biggest part of the distal portion 3.1 consists of two longitudinal extensions rather than a tube shape in order to allow other parts of the auto-injector 1 to engage in the housing 2 for preventing relative rotation. This could alternatively be achieved by a tubular distal portion 3.1 with longitudinal slots. A proximal portion 3.2 of the shroud 3 has a reduced diameter compared to the distal portion 3.1 for slidably accommodating a syringe carrier 4. The syringe carrier 4 holds a syringe 5 and supports it at its proximal end in order to avoid stress to its finger flanges 5.1. A hollow injection needle 6 is attached to the proximal end of the syringe 5. A stopper 7 serves for sealing the distal end of the syringe 5. A liquid medicament M stored in the syringe 5 may be displaced through the needle 6 by pushing the stopper 7 in proximal direction P by means of a plunger 8. In the as shipped state the syringe 5 and syringe carrier 4 are locked in position thus providing a clearance between the plunger 8 and the stopper 7. Although the needle 6 protrudes beyond the proximal end P of the auto-injector 1, needle stick injuries are avoided by a protective needle shield 9 attached to the needle 6 in the as shipped state. The syringe carrier 4 is biased in distal direction D with respect to the shroud 3 by means of a syringe spring 10 bearing against a shoulder 3.3 in the shroud 3 and against a rear flange 4.1 in the syringe carrier 4. The shoulder 3.3 is defined between the distal portion 3.1 and the proximal portion 3.2. The rear flange 4.1 is arranged at the distal end of the syringe carrier 4. A drive spring 11 is arranged near the distal end D of the auto-injector 1 inside the shroud 3. The drive spring 11 is preferably arranged as a compression spring. The distal end of the drive spring 11 is grounded in the housing 2 or in a grounding member 12 fixed to the housing 2. The proximal end of the drive spring 11 bears against a drive collar 13 which is arranged inside the drive spring 11, rotationally fixed by splines 2.4 in the housing 2 but translatable in longitudinal direction. Inside the drive collar 13 a drive sleeve 14 is arranged which in turn is arranged around the plunger 8. The drive sleeve 14 is rotationally free and axially fixed by distally bearing against the grounding member 12 and proximally bearing against a second bulkhead 2.2. The plunger 8 rotationally fixed and axially free. The drive collar 13 is engaged with the drive sleeve 14 by a first screw thread 15. The drive sleeve 14 is engaged with the plunger 8 by a second screw thread 16. Hence, when the drive collar 13 is pushed in proximal direction P by the drive spring 11, the drive sleeve 14 is caused to rotate which causes axial movement of the plunger 8. The first screw thread 15 and the second screw thread 16 are like-handed. By varying the pitch of the two screw threads 15, 16 a ratio of translation of the drive collar 13 and the plunger 8 is changed and hence the transmitted force is amplified or reduced.

The screw threads 15, 16 may have cam tracks and followers or ball bearings.

A syringe viewing window 17 for inspecting the syringe contents is provided in the proximal portion 3.2 of the shroud 3.

A housing cap 18 and a trigger button 19 are arranged at the distal end D of the auto-injector 1.

Figure 1C:
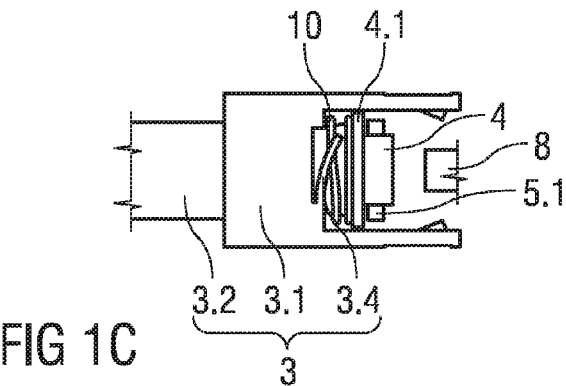

In the shipped state in FIG. 1, the drive spring's 11 preload on the drive collar 13 is statically resolved through distal snap arms 13.1 of the drive collar 13 which are engaged behind a shoulder 12.1 in the grounding member 12. The syringe carrier 4 is prevented from moving in proximal direction P by the rear flange 4.1 bearing against a first bulkhead 2.1 provided in the housing 2. Withdrawal of the shroud 3 into the housing 2 is resisted by flexural elements 3.4 on the shroud 3 acting against the first bulkhead 2.1 of the housing 2 from the proximal side (see FIG. 1c for details). Extension of the shroud 3 in proximal direction P is prevented by inward protrusions 3.5 contacting the drive collar 13. The syringe carrier 4 is locked to the shroud 3 by at least two snaps 4.2.

The protective needle shield 9 is interlocked to the syringe carrier 4. For this purpose the syringe carrier 4 has a pair of resilient snaps 4.2 extending proximally beyond the section of the syringe carrier 4 supporting the proximal end of the syringe 5. In the state as shipped these snaps 4.2 are snapped into corresponding recesses provided in the proximal portion 3.2 of the shroud 3 thus preventing relative axial translation between the shroud 3 and the syringe carrier 4. The snaps 4.2 are kept from flexing inwards and disengaging from the recesses by the protective needle shield 9. The protective needle shield 9 protrudes beyond the proximal end of the shroud 3 through an orifice.

Figure 2:
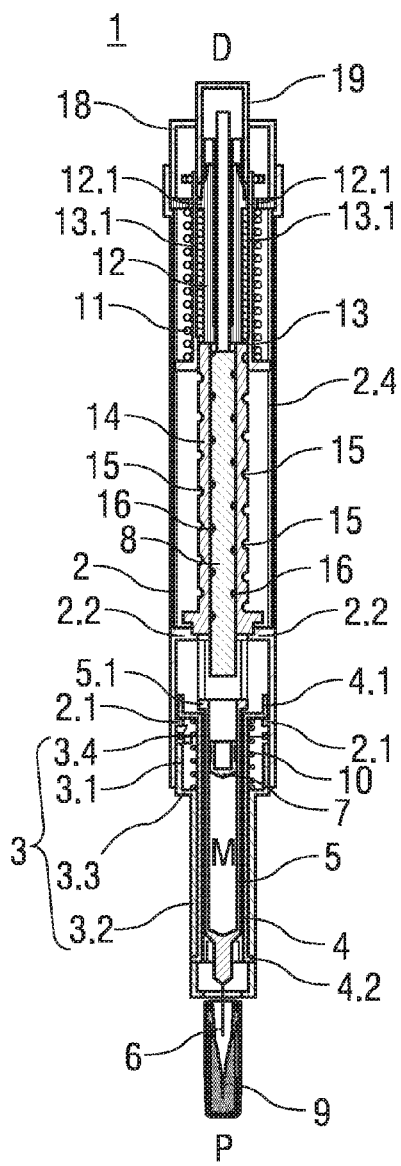
FIG. 2 is the auto-injector during removal of a protective needle shield.
Figure 3:
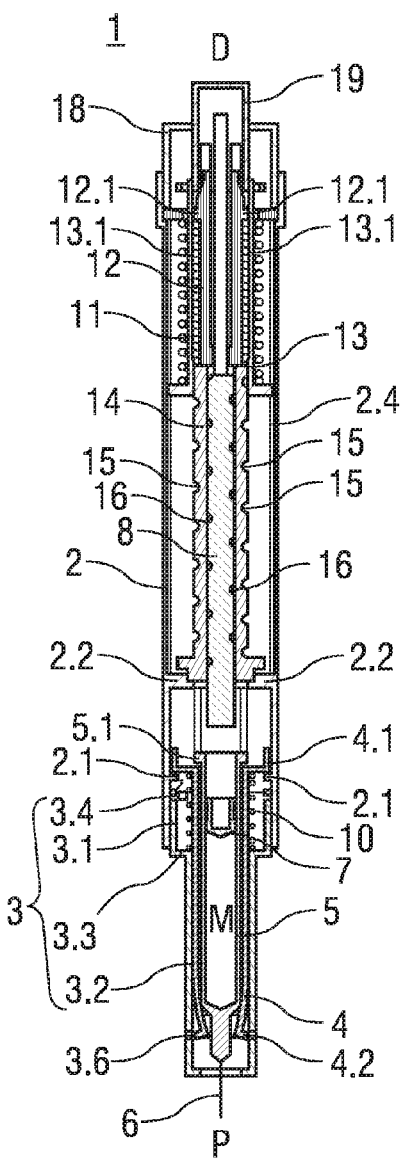
FIG. 3 is the auto-injector with a syringe carrier delatching from a shroud following the removal of the protective needle shield.

In order to arm the auto-injector 1 the protruding part of the protective needle shield 9 is gripped by a user and pulled off the syringe 5 and needle 6 in proximal direction P (see FIG. 2). Once the protective needle shield 9 has been removed the snaps 4.2 are no longer supported inwardly and disengage from the recesses 3.6 (see FIG. 3). Preferably the snaps 4.2 are biased to relax inwards when not supported. In an alternative embodiment the snaps 4.2 and the shroud 3 may have angled mating surfaces for moving the snaps 4.2 inward thus disengaging them from the recesses 3.6 under the force from the syringe spring 10 when the snaps 4.2 are not supported inwardly. In this case the snaps 4.2 do not have to be biased inwardly.

Figure 4A:
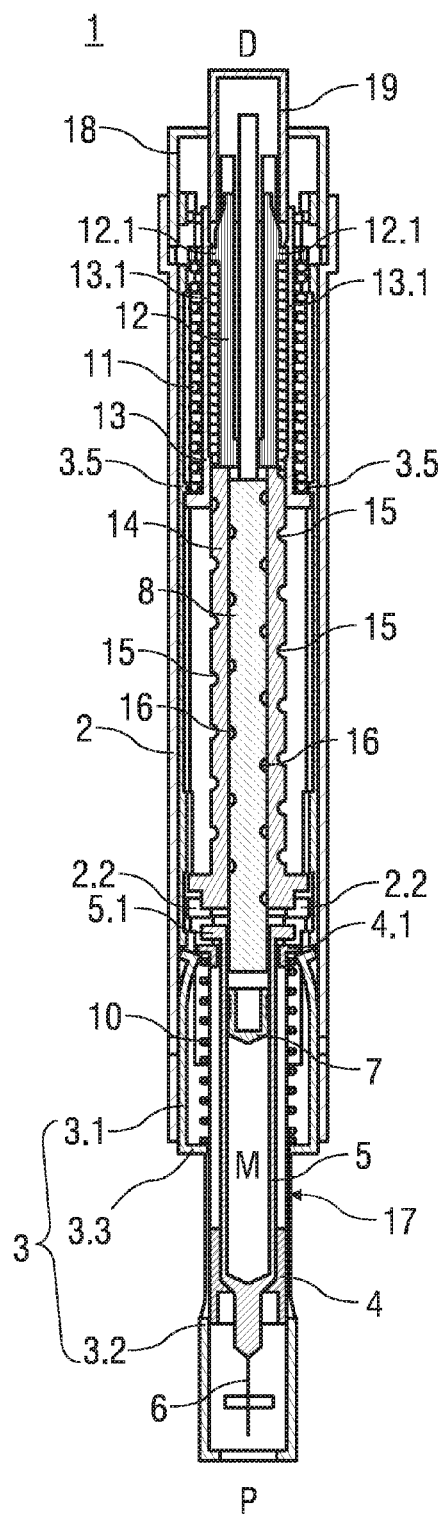
FIG. 4 is the auto-injector with the syringe carrier, syringe and a needle being retracted into the shroud after delatching.
Figure 4B:
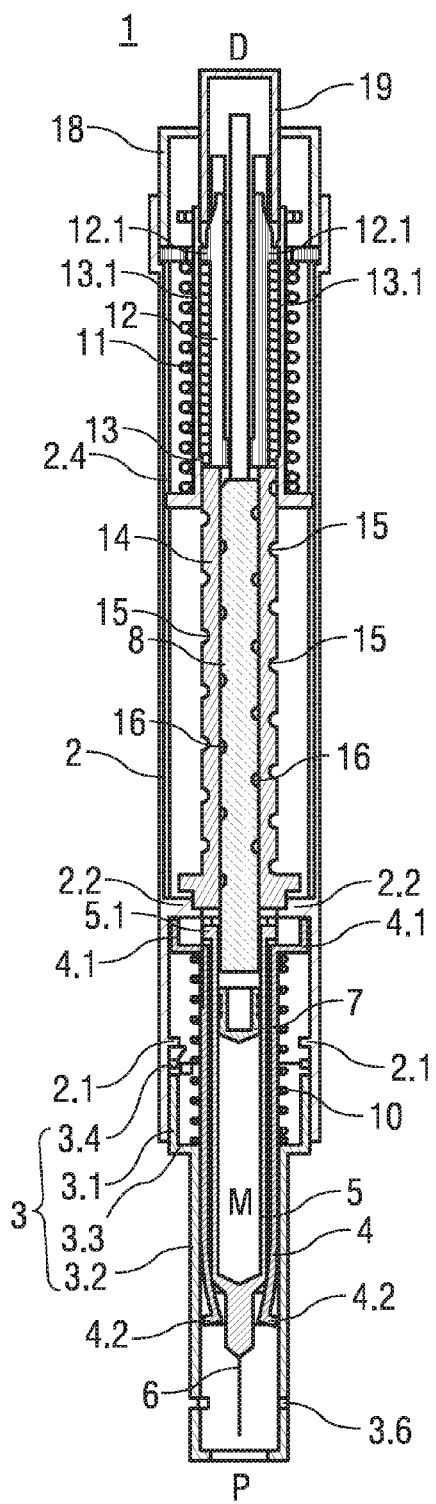

Now delatched from the shroud 3 the syringe carrier 4 together with the syringe 5 and the needle 6 are translated in distal direction D due to the load of the syringe spring 10 (see FIG. 4). Thus the needle 6 is hidden inside the shroud 3 and the user protected from accidental needle stick injuries.

Figure 5A:
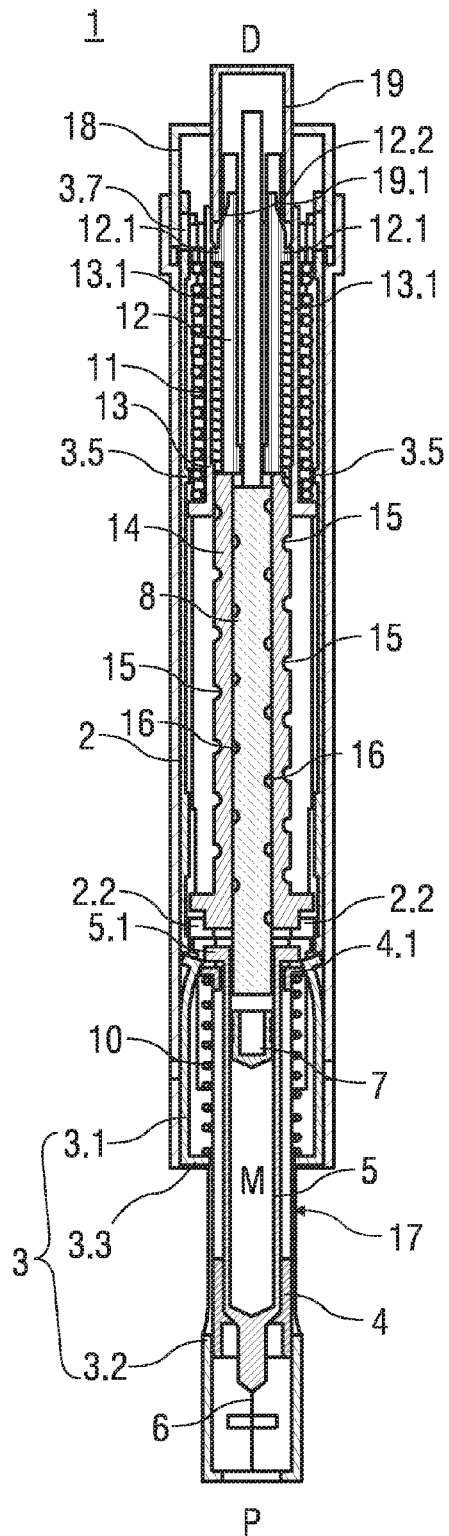
FIG. 5 is the auto-injector during deactivation of an interlock by pressing the shroud against an injection site.
Figure 5B:
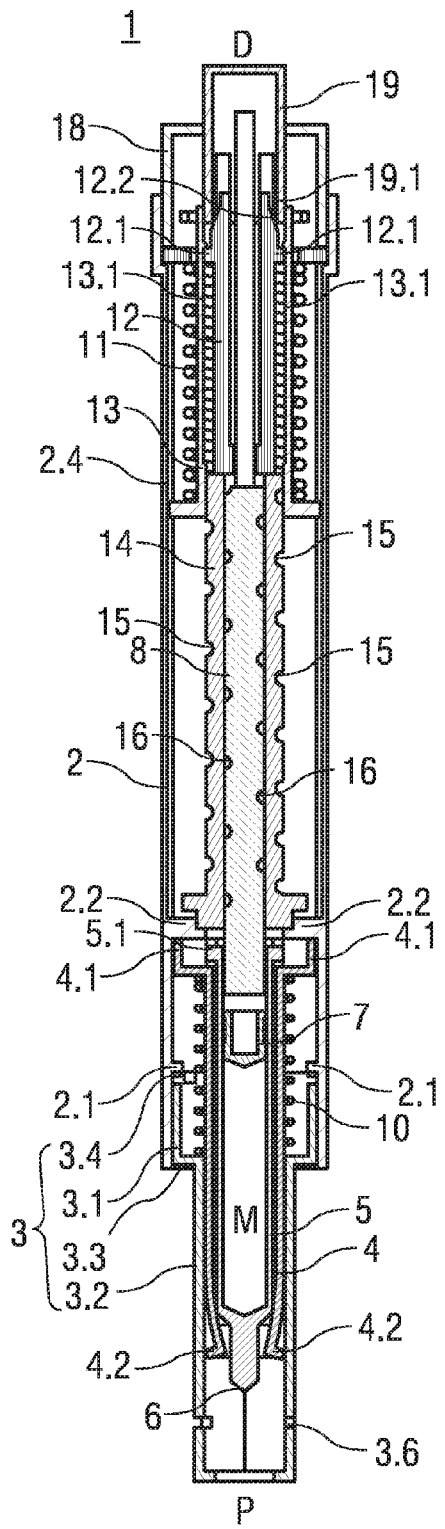
Figure 5C:
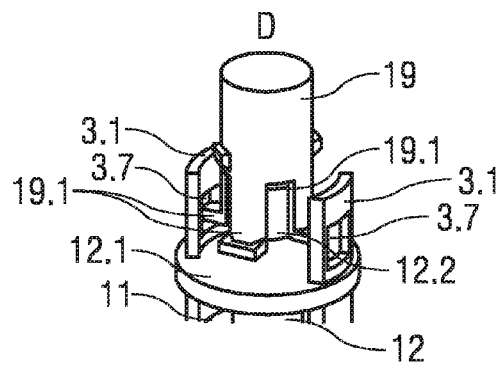

In the next operating step the user places the proximal end P of the auto-injector 1 against an injection site, e.g. a patient's skin. When contacting the injection site the shroud 3 is depressed and translates by a small distance in distal direction D into the housing 2 (see FIG. 5) against the load of the flexural elements 3.4. As the shroud 3 translates, apertures in the shroud 3 move from a blocking position against trigger button resilient extensions 19.1, thus unlocking the trigger button 19.

The trigger button 19 comprises a number of resilient extensions 19.1 facing the grounding member 12. The grounding member 12 has a tapering surface 12.2 facing the trigger button 19. The resilient extensions 19.1 are at least partially arranged inside the snap arms 13.1 of the drive collar 13. When the trigger button 19 is pushed in proximal direction P, the resilient extensions 19.1 contact the tapering surface 12.2 and are splayed apart. Consequently, the resilient snap arms 13.1 are also splayed apart and disengaged from the shoulder 12.1 of the grounding member 12. Thus, the drive collar 13 is no longer axially restricted and will be released in the proximal direction P by the drive spring 11.

Before the shroud 3 is depressed (FIGS. 1 to 4) the distal portion 3.1 of the shroud 3 prevents the trigger button's 19 resilient extensions 19.1 from splaying out. As the shroud 3 is depressed (FIG. 5) it travels in distal direction D to such an extend that the resilient extensions 19.1 meet respective distal recesses 3.7 thus allowing the resilient extensions 19.1 to be splayed apart (see FIG. 5c for details). At the same time the syringe spring 10 is partially compressed by depressing the shroud 3.

Figure 6A:
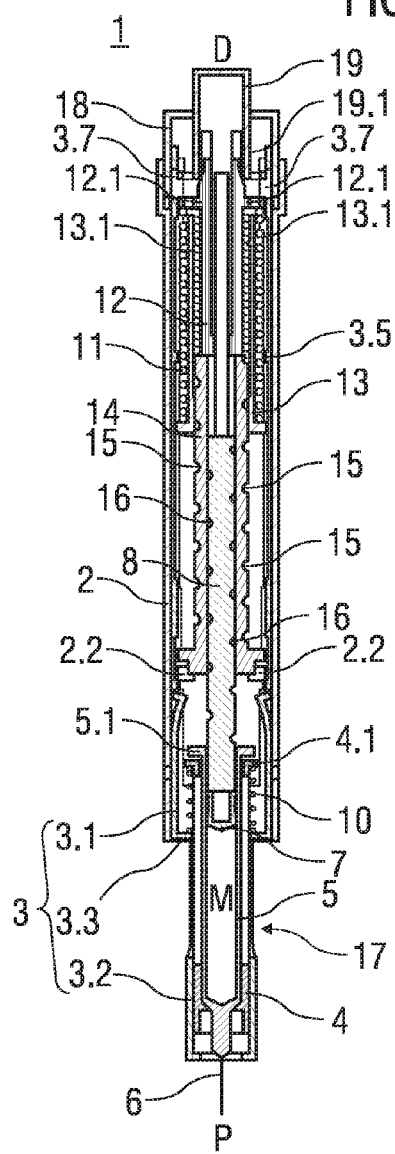
FIG. 6 is the auto-injector during needle insertion into the injection site.
Figure 6B:
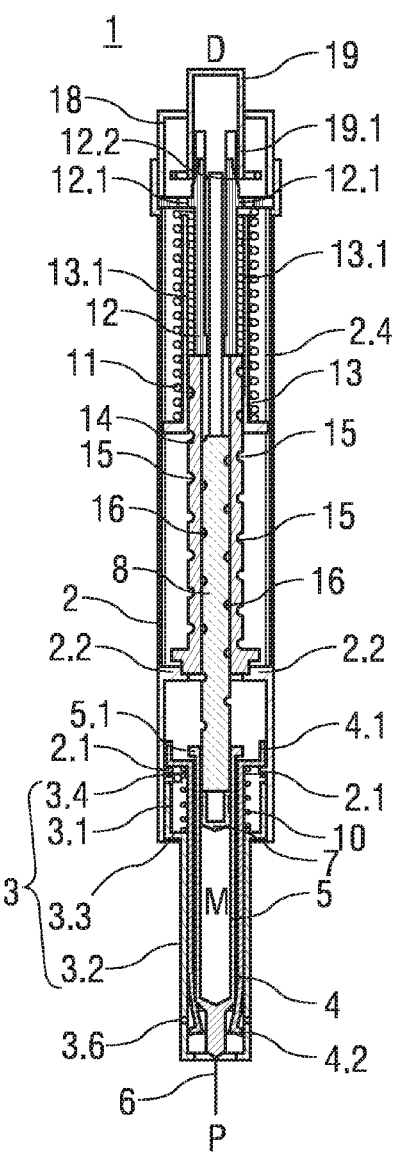

When the trigger button 19 is pressed and the drive collar 13 is delatched from the grounding member 12 the force of the drive spring 11 translates the drive collar 13 in proximal direction P (see FIG. 6). Rotation of the drive collar 13 is prevented by splined engagement in the housing 2. The drive sleeve 14 is forced to rotate by engagement to the drive collar 13 through the first screw thread 15. The plunger 8 extends towards the stopper 7 by engagement to the drive sleeve 14 through the second screw thread 16. The first screw thread 15 may comprise an external, right-handed screw thread in the drive sleeve 14 engaged with a ball located in a pocket on the internal surface of the drive collar 13. The second screw thread 16 may comprise an external right-handed screw thread in the plunger 8 engaged with a ball located in a pocket on the internal surface of the drive sleeve 14. Alternatively, both screw threads 15, 16 may be left-handed. Rotation of the plunger 8 is prevented by splined engagement in the grounding member 12. This may be achieved by corresponding non-circular cross sections, e.g. square cross sections.

The gear ratio of the gear box comprising the drive collar 13, the first screw thread 15, the drive sleeve 14 and the second screw thread 16 is defined by the pitch angles of the two screw threads 15, 16. If the pitch angle of the drive sleeve 14 is greater than that of the plunger 8, the gear ration will be greater than 1, i.e. the gear box acts as a distance multiplier. Conversely, when the plunger 8 pitch angle is greater than that of the drive sleeve 14, the gear ration will be less than 1, i.e. the gear box acts as a force multiplier.

In an alternative embodiment the drive sleeve 14 may have an internal screw thread engaged with the plunger 8 and the drive collar 13 may have an internal screw thread engaged with the drive sleeve 14.

As the plunger 8 travels forward it meets the stopper 7 and applies a force on it which is resolved through the syringe spring 10. The counteracting force of the syringe spring 10 during compression has to be greater than a counteracting force of the stopper 7 due to friction between the stopper 7 and the inner wall of the syringe 5 and due to the hydrostatic resistance of the liquid medicament M to be displaced through the hollow needle 6. As the syringe spring 10 is compressed the syringe carrier 4 travels in proximal direction P together with the syringe 5 and the needle 6. Hence, the needle 6 is inserted into the injection site. The injection depth is set by the rear flange 4.1 of the syringe carrier 4 contacting the first bulkhead 2.1.

When the rear flange 4.1 hits the first bulkhead 2.1 the force of the plunger 8 pushes the stopper 7 in proximal direction P thus displacing the liquid medicament M from the syringe 5 through the needle 6 and into the injection site. During injection of the medicament M, the pitch angles of the screw threads 15, 16 may vary in order to adapt the mechanical advantage of the gearbox.

FIGS. 7a and 7c show the auto-injector 1 during removal from the injection site in the course of an injection cycle. If this happens, the shroud 3 will extend to cover the needle 6 under load of the syringe spring 10. In parallel, internal splines 3.8 on the distal part 3.1 of the shroud 3 engage in teeth 14.1 on the outer surface of the drive sleeve 14. This prevents further rotation of the drive sleeve 14 and hence expansion of the plunger 8 and further emptying of the syringe 5. FIG. 7b shows the drive sleeve 14 and the shroud 3 during injection with the shroud 3 persistently pressed against the injection site. Hence, the splines 3.8 and teeth 14.1 do not engage and the drive sleeve 14 continues rotating. By contrast, FIG. 7c shows the drive sleeve 14 and the shroud 3 during removal of the auto-injector 1 from the injection site in the course of an injection cycle. The shroud 3 is translated in proximal direction P to an extent bringing the teeth 14.1 and the splines 3.8 into engagement.

Even though the forward extension of the shroud 3 is limited by the position of the drive collar 13, the auto-injector 1 is configured to provide needle safety at all stages of the operational cycle:

With a transmission ratio of 1 or less as illustrated, as the needle is inserted into the injection site, the drive collar 13 moves in sync with the syringe 5. Therefore, given that the needle 6 is initially fully covered when the shroud 3 is fully extended and the needle 6 moves in sync with the drive collar 13, the needle can not protrude a greater distance from the shroud 3 than the distance permitted by the drive collar 13 and the inward protrusions 3.5. If the transmission ratio were greater than 1, the design may be modified to position the needle 6 further from the proximal end of the shroud 3 to ensure needle safety at all stages of the injection.

Figure 8A:
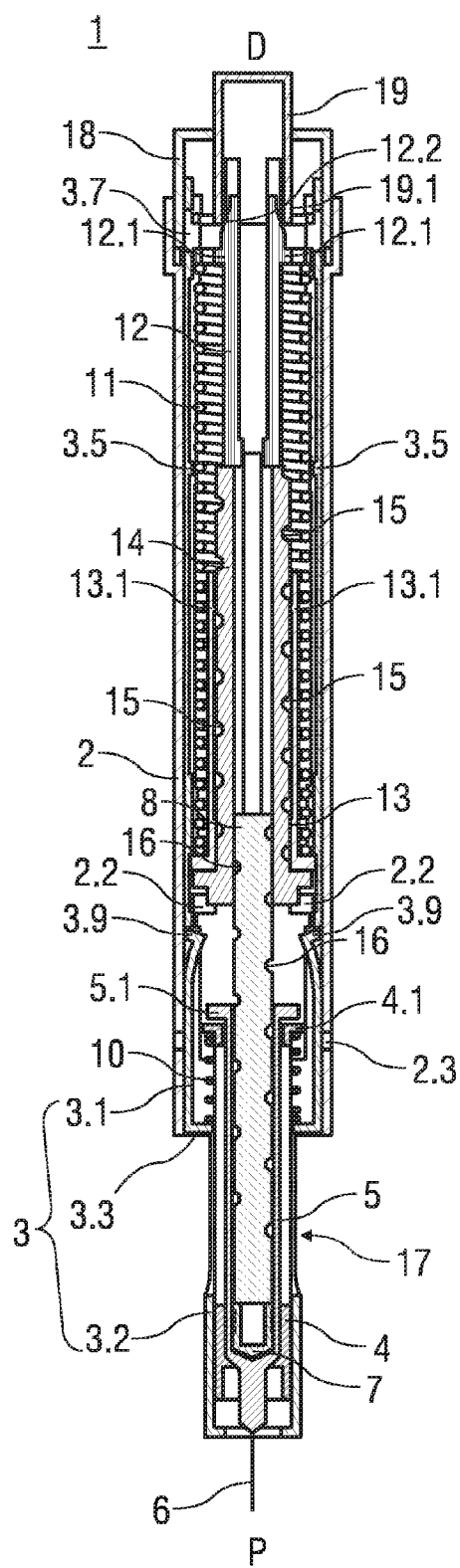
FIG. 8 is the auto-injector near the end of the injection.
Figure 8B:
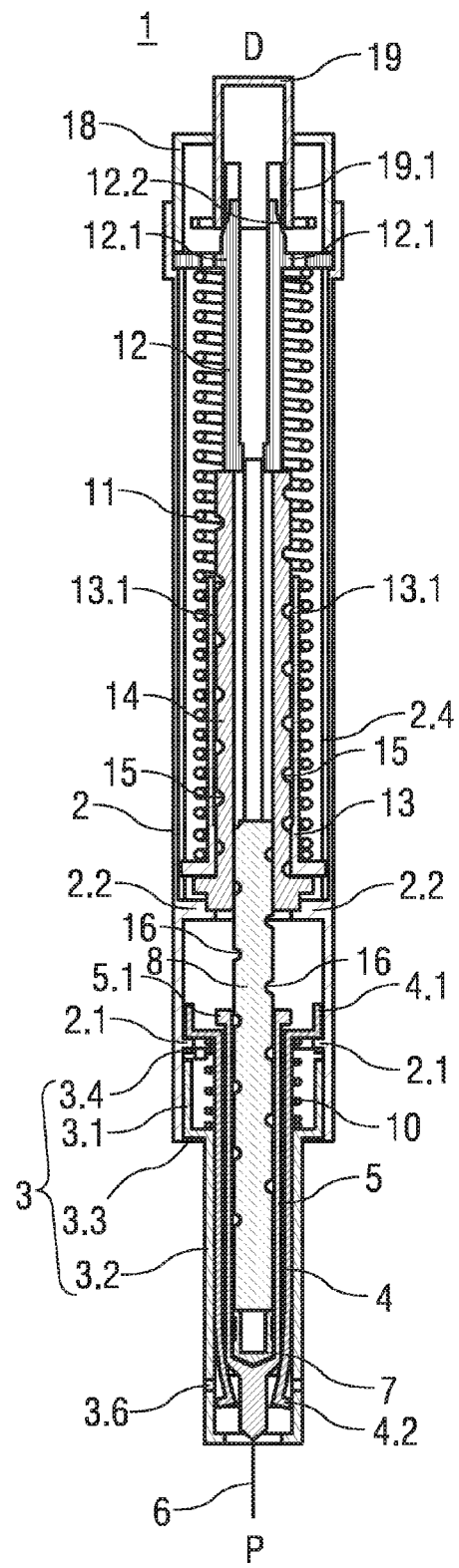

In FIG. 8 the stopper 7 has reached the end of the syringe 5 and the dose is fully delivered. The auto-injector 1 is sized so that this occurs prior to the drive collar 13 and/or plunger 8 reaching end-of-travel on their respective screw threads 15, 16, in particular before a flange 13.2 of the drive collar 13 contacts a flange 14.2 of the drive sleeve 14. The end of dose may be indicated to the user by an elapsed time (e.g. ten seconds), visible inspection through the syringe viewing window 17, or audible detection of movement of a ratchet engaged between any two parts with relative motion, for example the housing 2 and the drive sleeve 14.

Figure 9:
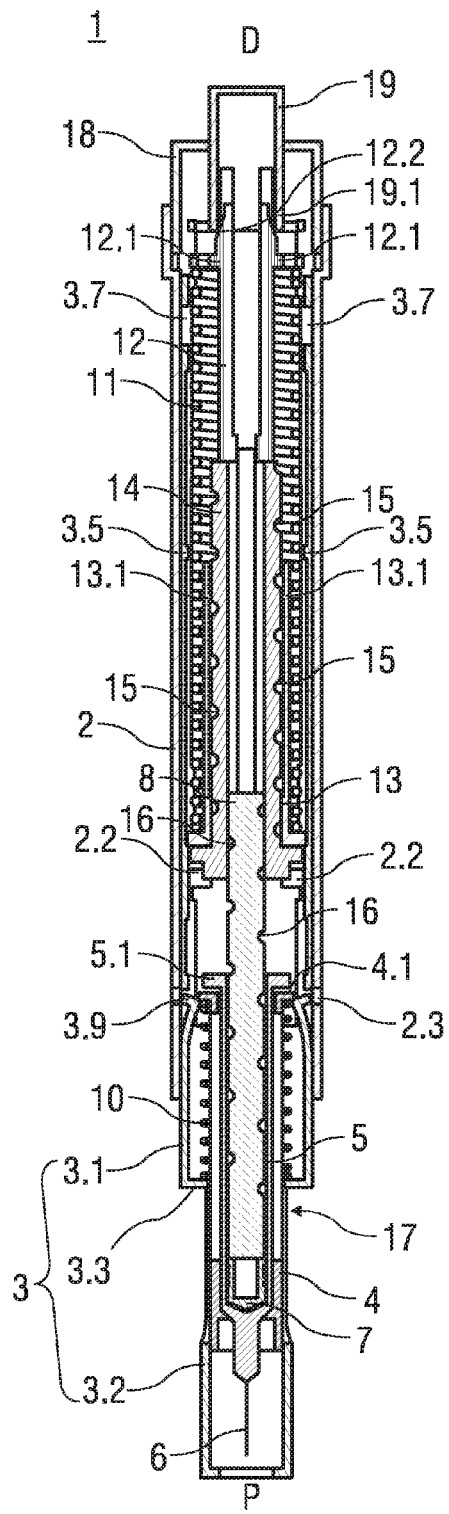
FIG. 9 is the auto-injector withdrawn from the injection site after having completed the injection, wherein the shroud extends to cover the needle.

When the dose has been fully delivered the user may remove the auto-injector 1 from the injection site thus extracting the needle 6. As the auto-injector 1 is removed, the shroud 3 extends under bias of the syringe spring 10 (see FIG. 9).

Figure 10:
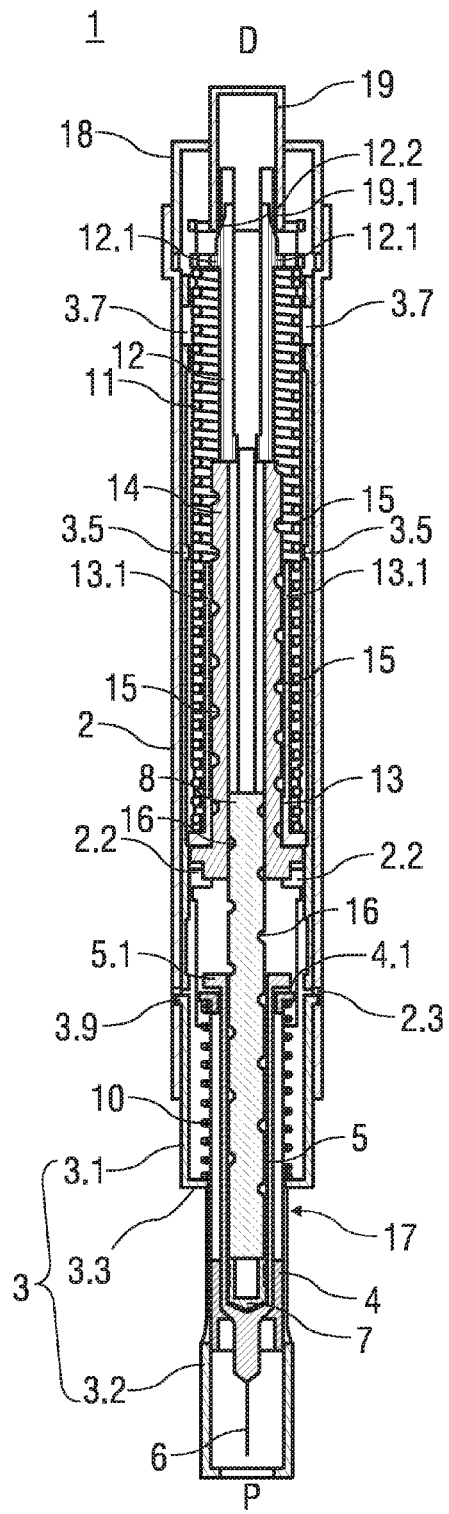
FIG. 10 is the auto-injector with the shroud locking into the housing.

When the shroud 3 is at least almost fully extended, resilient latches 3.9 in the distal portion 3.1 of the shroud 3 snap into respective recesses 2.3 arranged in the housing 2 thus preventing the shroud 3 from being pushed in distal direction D again, so post injection needle safety is provided (FIG. 10). This applies for both cases, when the auto-injector 1 is removed from the injection site during injection (FIG. 7a) or after delivering the full dose (FIG. 8).

The syringe carrier 4 has lateral apertures corresponding to the syringe viewing window 17 in order to allow visual inspection of the syringe 5.

Figure 11:
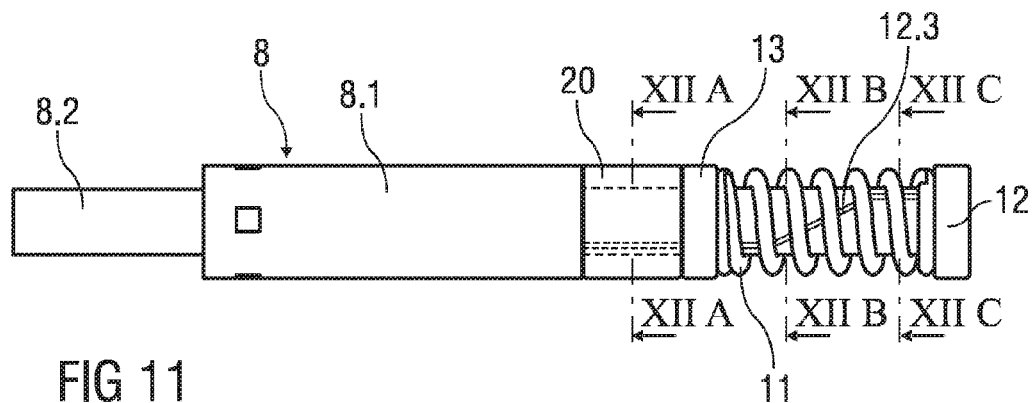
FIG. 11 is a lateral view of a detail of an alternative embodiment of an auto-injector with force control with a friction collar, FIG. 12 are three cross sections of the detail of FIG. 11.
Figure 12A:
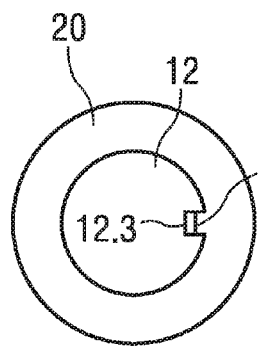
Figure 12B:
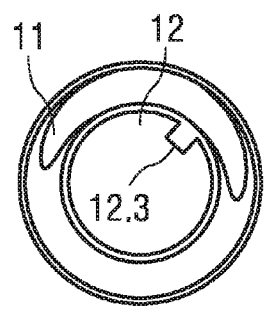
Figure 12C:
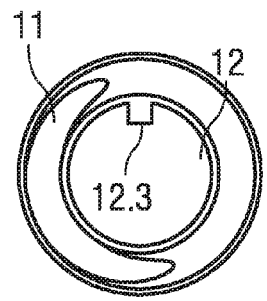
Figure 13:
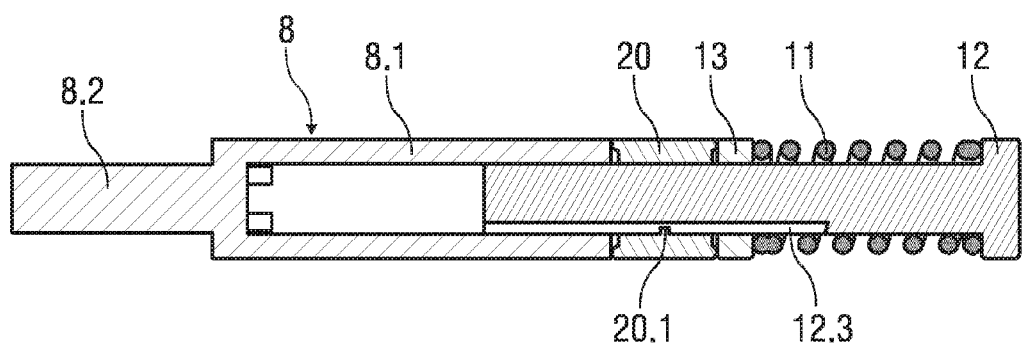
FIG. 13 is a longitudinal section of the detail of FIG. 11.

In another embodiment the gearbox as shown in the preceding figures comprising the drive collar 13, the first screw thread 15, the drive sleeve 14 and the second screw thread 16 may be replaced by a rotary friction element shown in FIGS. 11 to 13. The rotary friction element comprises a friction collar 20. In this embodiment the drive spring 11 bears against the drive collar 13 which in turn pushes against the friction collar 20 in sync with the plunger 8. At predetermined times the friction collar 20 is forced to rotate by its engagement in a cam track 12.3 provided in the grounding member 12. For this purpose the friction collar 20 has a cam follower 20.1.

As in the gearbox (FIG. 1) the drive collar 13 is rotationally fixed and axially free. The friction collar 20 in contrast is axially free and rotationally constrained by friction and by the cam track 12.3. The plunger 8 comprises a hollow distal portion 8.1 fitting onto a shaft of the grounding member 12 and a proximal portion 8.2 with a reduced diameter. The cross sections of both the hollow distal portion 8.1 and the shaft of the grounding member 12 may be designed to prevent rotation of the plunger 8. For instance the plunger 8 may have a cam follower running in a straight section of the cam track 12.3. Rotation of the friction collar 20 is defined by the cam track 12.3. The load on the friction collar 20 is coupled to the rotationally fixed, axially free plunger 8 which applies a force to the stopper 7. The compressive force of the drive spring 11 acting on both mating surfaces of the friction collar 20 towards the drive collar 13 and towards the plunger 8 introduces a friction force opposing rotation. As the friction collar 20 axially translates, it is forced to rotate by any section of the cam track 12.3 that is not parallel with the longitudinal axis of the auto-injector 1. The friction collar 20 will only rotate if the friction force between the mating surfaces of the drive collar 13 and the plunger 8 is overcome. The torque to overcome this friction force is generated by the contact force between the cam follower 20.1 and the cam track 12.3, in which the cam follower 20.1 is engaged. The contact force is generated by the spring force of the drive spring 11. A degree of coupling between the spring force and the contact force is defined by the respective angle of the cam track 12.3. By an appropriate modification to the cam track angle, the amount of spring force required to overcome the friction force can be modified. For instance, increasing the cam angle requires more of the spring force to be reacted through the cam track 12.3, thereby reducing the force applied to the stopper 7.

In an alternative embodiment an intermediary component may be provided for first coupling the plunger 8 to the syringe carrier 4 or the syringe 5 directly without acting on the stopper 7 until the needle 6 has reached its injection depth. The plunger 8 would then be decoupled from the syringe 5 or syringe carrier 4 by the intermediary component and instead be coupled to the stopper 7 in order to displace the medicament M from the syringe 5. Thus, wet injection is avoided, i.e. the medicament is not leaking out of the needle tip before the needle is inserted. The intermediary component may be a transfer sleeve or an additional feature at the syringe carrier 4. The transfer sleeve and plunger 8 would be initially coupled and translate together. However, when the syringe carrier 4 nears the end of its travel during needle insertion, the transfer sleeve would decouple from the plunger. From this point forwards, the plunger 8 load would be transferred directly to the stopper 7. This decoupling arrangement may be embodied in any suitable auto-injector arrangement. For example, the transfer sleeve could be clipped to the plunger by some clips. Near the end of travel the clips could find some place to splay or be pushed away from the plunger 8 in order to decouple the plunger 8 from the transfer sleeve.

LIST OF REFERENCES 1 auto-injector
2 housing
2.1 first bulkhead
2.2 second bulkhead
2.3 recess
2.4 spline
3 shroud
3.1 distal portion
3.2 proximal portion
3.3 shoulder
3.4 flexural element
3.5 inward protrusion
3.6 recess
3.7 distal recess
3.8 spline
3.9 latch
4 syringe carrier
4.1 rear flange
4.2 snap
5 syringe
5.1 finger flange
6 needle
7 stopper
8 plunger
8.1 distal portion
8.2 proximal portion
9 protective needle shield
10 syringe spring
11 drive spring
12 grounding member
12.1 shoulder
12.2 tapering surface
12.3 cam track
13 drive collar
13.1 snap arm
13.2 flange
14 drive sleeve
14.1 tooth
14.2 flange
15 first screw thread
16 second screw thread
17 syringe viewing window
18 housing cap
19 trigger button
19.1 resilient extension
20 friction collar
20.1 cam follower
D distal end, distal direction
M medicament
P proximal end, proximal direction

The invention claimed is:

1. Transmission arrangement for controlling a force of a translation of a plunger of an injection device, the transmission arrangement comprising a drive collar connected to a translative drive means and prevented from rotating with respect to a ground of the drive means, a flange face of the drive collar bearing against a mating flange face of a friction collar, the friction collar slidable in longitudinal direction and rotationally constrained by engagement in a cam track comprising at least one section having a non-zero pitch angle, another flange face of the friction collar bearing against a mating flange face of a plunger, the plunger slidable in longitudinal direction and prevented from rotating.

2. Transmission arrangement according to claim 1, characterized in that the drive means is a compression spring arranged on a shaft of a grounding member, wherein the drive collar and the friction collar are arranged in series with the compression spring on the shaft, wherein the cam track is arranged in the shaft and wherein a cam follower for engaging in the cam track is arranged at the friction collar.

3. Transmission arrangement according to claim 1, characterized in that a pitch angle of the cam track is varied over its length.

4. Transmission arrangement according to claim 1, characterized in that the cam track comprises at least one straight, longitudinal section.

5. Transmission arrangement according to claim 2, characterized in that the plunger comprises at least a hollow portion arranged for fitting onto the shaft.

6. Transmission arrangement according to claim 5, characterized in that the plunger comprises a cam follower for engaging in one of the straight, longitudinal sections of the cam track.

7. Transmission arrangement according to claim 1, characterized in that the mating faces on the friction collar and the plunger are profiled so as to increase or reduce a distance traveled by the plunger relative to the motion of the drive collar by modifying an overall length of the drive collar, friction collar and plunger when the friction collar is rotated.

8. Auto-injector for administering a dose of a liquid medicament (M), the auto-injector having a distal end (P) and a proximal end (D) with an orifice intended to be applied against an injection site and comprising:
an elongate housing arranged to contain a syringe with a hollow needle and a stopper for sealing the syringe and displacing the medicament (M), wherein the syringe (5) is slidably arranged with respect to the housing,
a drive means capable of, upon activation:
pushing the needle from a retracted position into an advanced position through the orifice and past the proximal end (P), and
operating the syringe to supply the dose of medicament (M), and activating means arranged to lock the drive means in a pressurized state prior to manual operation and capable of, upon manual operation, releasing the drive means for injection, characterized in that a transmission arrangement according to claim 1 is arranged between the drive means and the syringe or the stopper.

9. Auto-injector according to claim 8, characterized in that an intermediary component is arranged for transmitting translation of the plunger to the syringe for advancing the syringe and the needle and wherein the intermediary component is arranged to be decoupled from the syringe and to couple the translation to the stopper when the needle reaches a defined injection depth.

10. Auto-injector according to claim 8, characterized in that a shroud is arranged at least partially inside the housing, the shroud slidable in longitudinal direction between at least a retracted position, in which the needle is exposable and an advanced position, in which the needle is covered by the shroud, wherein the shroud is arranged to be locked in the retracted position prior to manual operation of the activation means and wherein the shroud is arranged to be pushed towards the advanced position by a syringe spring when the drive means has been released.

11. Auto-injector according to claim 9, characterized in that the shroud is slidable from the retracted position in distal direction (D) into an unlocking position by a small distance against the bias of at least one flexural element, wherein interlocking means are arranged to allow the activating means to be operated only, when the shroud is in the unlocking position, wherein the interlocking means are arranged to prevent the activating means from being operated otherwise.

12. Auto-injector according to claim 10, characterized in that a protective needle shield is attachable to the needle in a manner to partially protrude beyond the proximal end of the shroud through the orifice with the needle in its advanced position, wherein a syringe carrier is arranged inside the shroud for holding the syringe, the syringe carrier slidable with respect to the shroud, wherein the syringe carrier comprises at least one resilient snap for lacking it to the shroud in order to prevent relative axial motion, wherein the snap is arranged to be supportable from inside by the protective needle shield when attached to the needle in order to remain engaged with the shroud and wherein the snap is inwardly biased to disengage from the shroud without support from inside in a manner to automatically disengage upon removal of the protective needle shield thus allowing the syringe and needle to be refracted into the retracted position under load of the syringe spring.

13. Auto-injector according to claim 10, characterized in that at least one resilient latch is arranged at the shroud for engaging in a respective recess of the housing when the shroud is translated into its advanced position.

14. Auto-injector according to claim 11, characterized in that at least one snap arm is distally arranged at the drive collar in a manner to be engageable behind a shoulder on the grounding member in order to prevent expansion of the drive means, the snap arm disengageable from the shoulder by being pushed outward by a respective resilient extension of a trigger button, the resilient extension arranged to be flexed outward by pushing the trigger button in proximal direction (P) thereby moving the resilient extension along a tapering surface of the grounding member, wherein the shroud is arranged to prevent at least one of the resilient extensions from flexing outwards when in the retracted position and wherein at least one distal recess is arranged in the shroud for allowing a respective resilient extension to be flexed outwards when the shroud is in its unlocking position.

15. Auto-injector according to claim 10, characterized in that the syringe spring bears against a shoulder in the shroud arranged between a distal portion and a proximal portion and against a rear flange of the syringe carrier.

\* \* \* \* \*